United States Patent [19]

Angstadt et al.

[11] 4,182,909

[45] Jan. 8, 1980

[54] POLYMERIC CATALYST COMPOSITION FOR HYDROCARBON OXIDATION

[75] Inventors: Howard P. Angstadt, Media, Pa.; John P. Bare, Wilmington, Del.

[73] Assignee: Sun Ventures, Inc., St. Davids, Pa.

[21] Appl. No.: 640,082

[22] Filed: Dec. 12, 1975

Related U.S. Application Data

[60] Continuation-in-part of Ser. No. 451,717, Mar. 14, 1974, abandoned, which is a division of Ser. No. 217,945, Jan. 14, 1972, abandoned.

[51] Int. Cl.$^2$ .......................................... C07C 179/02
[52] U.S. Cl. .................................................. 568/574
[58] Field of Search .................... 260/610 B; 568/574

[56] References Cited

U.S. PATENT DOCUMENTS

| | | | |
|---|---|---|---|
| 2,821,512 | 1/1958 | Haven | 260/2 M |
| 3,242,102 | 3/1966 | Schmeckenbecher | 260/2 M |
| 3,242,105 | 3/1966 | Waack | 260/2 M |
| 3,803,243 | 4/1974 | Brownstein et al. | 260/610 B |

*Primary Examiner*—Warren B. Lone
*Attorney, Agent, or Firm*—J. Edward Hess; Donald R. Johnson; Stanford M. Back

[57] ABSTRACT

Novel polymeric compositions and processes for employing the same as autoxidation catalysts in the oxidation of olefins and secondary and tertiary alkylaromatic compounds are provided herein. These novel compositions comprise organometallic compounds wherein the organic compositions comprise organometallic compounds which incorporate in the backbone or on side groups in the polymer polar units capable of binding suitable metal ions which together form the oxidation catalyst.

11 Claims, No Drawings

4,182,909

POLYMERIC CATALYST COMPOSITION FOR HYDROCARBON OXIDATION

RELATED APPLICATIONS

This application is a continuation-in-part of U.S. Ser. No. 451,717, filed Mar. 14, 1974 now abandoned by Howard P. Angstadt and John P. Bare, which in turn is a divisional application of U.S. Ser. No. 217,945, filed Jan. 14, 1972 (now abandoned), said latter case having been refiled as a continuation-in-part, U.S. Ser. No. 482,920, now U.S. Pat. No. 3,890,281, issued June 17, 1975.

The subject matter of the instant invention is closely related to the following pending applications, and patents, all of which belong to a common assignee of the present inventor and the inventors listed below:

| Serial/Patent No. | Filing Date | Inventor(s) | Title |
|---|---|---|---|
| 525,892 | 11/21/74 | Angstadt, et al. | Organometallic Complexes and Alkylaromatic Oxidation Catalysts |
| 524,910 | 11/18/74 | Angstadt | Organometallic Complexes and Alkylaromatic Oxidation Catalysts |
| 526,036 | 11/21/74 | Angstadt, et al. | Oxidation of Olefins with Organometallic Complex Catalysts |
| 524,911 | 11/18/74 | Angstadt | Organometallic Complexes as Oxidation Catalysts |
| 525,548 | 11/20/74 | Angstadt | Organometallic Complexes as Oxidation Catalysts |
| 524,912 | 11/18/74 | Angstadt | Catalyst Composition for Oxidation |
| 3,836,589 | 9/24/69 | Angstadt | Improved Method for Oxidation of Hydrocarbons |

BACKGROUND OF THE INVENTION

This invention relates to a novel composition and method for using the same as catalysts in the oxidation of hydrocarbons. More particularly, this invention relates to the oxidation of compounds such as olefins and secondary and tertiary alkylaromatic hydrocarbons to form the corresponding hydroperoxides or like oxidation products, wherein there is employed as the autoxidation catalyst novel organometallic compounds having polymeric backbones.

In the above-mentioned related cases, Ser. Nos. 525,892; 524,910; 526,036; 524,911; 525,548; and 524,912, filed in the name of Angstadt (et al.), there is disclosed a series of organometallic autoxidation catalysts comprising such ligands as hexaalkylphosphoramides, trialkylphosphates, dialkylsulfoxides, tetraalkylureas, and the like, as well as thermally condensed polyacrylonitrile, complexed with metal ions selected from various groups of the Periodic Table. However, as shown in the last-mentioned case above, U.S. Pat. No. 3,836,589, each of these as well as other related organometallic catalysts is generally characterized by being very sensitive to water formed during the course of the oxidation, i.e., hydrolytic instability, which rapidly deactivates the catalyst. While the use of a dessicant, as taught in this latter case satisfactorily avoids this problem, nevertheless, the providing of a solid, insoluble catalyst which is both hydrolytically stable and easily recoverable, as contrasted with the more soluble organometallic complexes listed above, would be highly desirable. Not only would such catalyst have a longer life and be more readily recoverable, but also the need for the added dessicant would be avoided.

U.S. Pat. Nos. 2,821,512; 3,242,102; and 3,242,105 illustrate polymeric compounds containing bonded into their polymeric backbone structure various metals. However, in each case, these metals are so completely bonded to the polymer structure that they are sterically hindered and cannot function as catalytic agents.

SUMMARY OF THE INVENTION

It has now been found, in accordance with the present invention, that certain polymers, which contain in their backbone or as pendant side chains those functional groups capable of complexing with metal ions, can form together with these metal ions, valuable autoxidation catalysts for the oxidation of compounds containing activated carbon-hydrogen bonds such as olefins or secondary or tertiary alkylaromatic compounds to produce the corresponding hydroperoxides and/or the decomposition products thereof, i.e. aldehydes, ketones, alcohols, acids, and the like. These resulting polymers have been found to be more hydrolytically and/or thermally stable than corresponding non-polymeric organometallic catalysts. Moreover, since these polymers are insoluble under the conditions of this process, they are much more readily recoverable than the previously known soluble catalyst complexes.

By the term "activated carbon-hydrogen bonds" is meant those hydrogen-containing atoms in aliphatic groups such as methylene or methine groups which are adjacent to certain activating groups as defined more fully hereinbelow.

PREPARATION OF THE POLYMERIC CATALYSTS

The catalysts of this invention may be prepared in accordance with the disclosure in the parent copending application now U.S. Pat. No. 3,890,281. That is to say, in general, the novel catalysts of this invention are composed of two components, viz., (1) a polymer having functional groups either (a) incorporated in the polymeric backbone or (b) as pendant groups attached to said polymeric backbone; and (2) metal ions complexed solely with said functional groups. By definition, since the metal ions are attached only to the pendant functional groups, they do not form an integral portion of the polymer backbone, and are thus sterically exposed, thereby facilitating their function as catalytic agents. Moreover, it is not necessary that every functional group within the polymer contain a complexed metal ion. By the term "functional groups" is meant those groups in the polymer which are capable of complexing with metal ions and usually these groups will possess one or more hetero atoms from the group consisting of O, S, N, P, Cl, and Se.

These aforementioned polymeric catalysts may be prepared in one of two ways: (1) by polymerizing, in the presence of a metal ion, compounds capable of forming a polymer which contains the desired functional groups in the backbone or as pendant groups; or (2) more preferably, by preforming the abovedefined polymer and thereafter (a) fusing it with the metal ion, or (b) dissolving the pre-formed polymer in a suitable solvent and adding the desired metal ions to the solution.

The polymers employed in forming the catalysts of this invention are generally prepared by polymerizing together one or more monomers according to well-known polymerization techniques such that the resulting polymeric structure (i.e., backbone) contains as a repeating unit functional groups capable of forming complexes with metal ions. It will be noted, however, as mentioned above, that said metal ions are not an integral part of the polymer itself, but do comprise an essential part of the ultimate catalyst. It is equally possible to prepare suitable polymers by known polymerization techniques wherein the polymeric backbone itself does not contain the coordinating functionalities for metal ions, but rather these functional groups reside instead in pendant side chains.

An example of the first type (and in no way intended to be restrictive) of polymer preparation may be condensation polymerization as illustrated in equation (A).

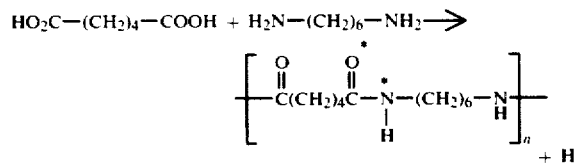

*Points for metal ion complexation

The second type of polymer preparation (addition polymerization) is illustrated by equation (B).

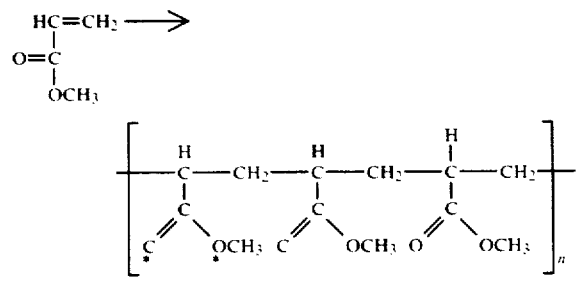

*Points for metal ion complexation

It will be understood, however, that there is no critical combination of compounds required for the formation of these polymers other than those dictated by the chemistry for their formation, and all that is essential is that the resulting polymers contain functional groups capable of forming complexes with the metal ions described below, and that the polymer be insoluble under the reaction conditions of the autoxidation process.

Typical amongst the functional groups which are capable of complexing with a suitable metal ion include those organic radicals having the partial structural formulas:

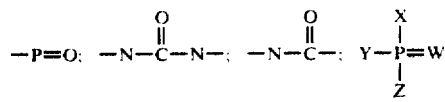

where X, Y, Z may be lower alkyl, aryl, alkoxy, thio, amino, cycloalkyl, seleno, etc. groups (or mixtures thereof), and W, O, N or S. Compounds from which these functional groups may be derived include alcohols, phenols, thiols, amines, alkyl halides, olefins and the like.

Monomers which may be combined with the aforesaid compounds to form the polymers of this invention include such compounds as styrene, vinyl alcohol, urea, ethylene diamine, and the like.

The source of the metal ions is most preferably metal salts which are derived from transition metals of Group IIIB, IVB, VB, VIB, VIIB, VIIIB, IB, IIA or IIB of the Periodic Table, including the lanthanide and actinide metals. Particularly effective are such metals as Co, Fe, Ni, Mn, Cu, Ag, Pd, Pt, Rh, Mo, Pr, La, Cs, Nd and Gd, of which Cu, Ni, Co, Fe and Nd are preferred. The enions of these salts may be any inorganic groups, although the chloride, bromides, nitrates, perchlorates and carbonates are generally preferred.

The formation of the polymer-metal salt complex requires no critical conditions or ratios of components, and may conveniently be achieved by any method known to those skilled in the art. Thus, for example, when the polymer is to be formed in the presence of the metal ions, this may conveniently be achieved by simply admixing stoichiometric quantities of the desired metal salt with a compound (or compounds) which will provide complexing sites in the resulting polymer, heating the mixture for a time sufficient for the polymer to form, and thereafter pulverizing, washing and drying the polymer to provide the catalyst of this invention. It will be understood that when a polymerizable monomer is used in combination with a compound which will provide functional groups in the resulting polymer, the ratio of these two compounds may be varied by those skilled in the art in order to obtain the number of reactive sites desired. Generally, however, it has been found that mole ratios of the two components in the range of 1:3 to 3:1, and preferably 2:1 to 1:2 are most suitable.

Alternatively, the polymer may be formed as above, but without the metal salt, followed by its fusion with the metal salt, in which case, as above, stoichiometric quantities of salt and polymer are heated together at temperatures of from about 100° C. to 500° C., depending upon the fusion temperature of the polymer, and preferably 150° C. to 300° C. for periods of about 1 hour to 5 hours. Thereafter, the same procedures of pulverizing, washing and drying the resultant polymer may conveniently be employed.

The following examples are illustrative of the preparation of some of the novel autoxidation catalysts used in the process of this invention.

POLYMER PREPARATION FOR USE IN FUSION-TYPE CATALYSTS PREPARATION

Example 1

Phenylphosphonic Dichloride-urea Polymer:

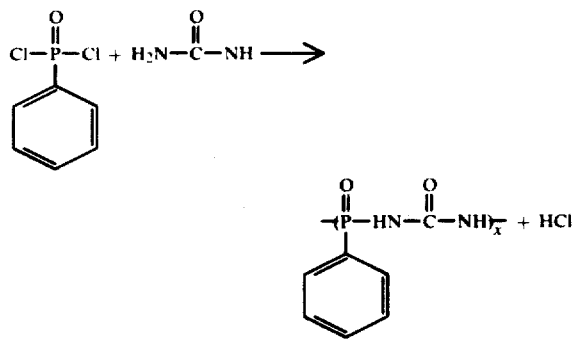

To 3.15 g. of urea in a 50 ml. flask equipped with a condenser is added 9.75 g. of phenylphosphoric dichloride. The mixture is heated to 110° C. for 45 minutes and stirred with a magnetic stirring bar until the material becomes too viscous to stir. The temperature is then raised to 255° C. for 1½ hours at atmospheric pressure and for an additional 178 hour at reduced pressure to facilitate removal of the product HCl. The solid is ground to a fine powder, washed with ether and dried. An elemental analysis of this material gives: C, 45.00; H, 4.25; N, 15.80; P, 16.5. The calculated values for the repeating unit shown above are: C, 46.1; H, 3.85; N, 15.4; P, 16.6.

A catalyst is prepared from the above polymer by heating 1 g. of the polymer to 270° C. for 2½ hours with 0.72 g. of anhydrous nickel dichloride. The product from this reaction is extracted with water in a Soxhlet extractor for four hours to remove the excess salt, then filtered and dried overnight in a vacuum dessicator.

Example 2

Phenyldichlorophosphine-urea Polymer:

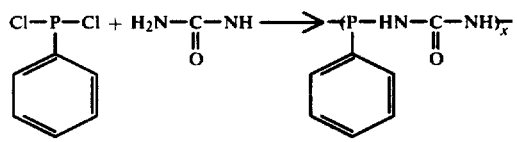

In accordance with the procedure described in Example 1, a polymer is prepared by reacting 8.95 gms. of phenyldichlorophosphine with 3.15 gms. of urea at 110° C. for 45 minutes. The temperature is then raised to 255° C. for 1½ hours at atmospheric pressure and for an additional ½ hour at reduced pressure to facilitate removal of HCl. The solid obtained on cooling is ground to a fine powder, washed with ether and dried. An elemental analysis of this product gives: C, 44.45; H, 4.58; N, 16.30. The values calculated from the above repeating units are: C, 50.6; H. 4.22; N, 16.9.

Also in accordance with the procedures of Example 1, when 1.0 gm. of the above polymer is heated with 7.5 gms. of anhydrous nickel dichloride, the resulting product may be worked up to provide the corresponding nickel catalyst.

Example 3

Phosphonyl-urea Polymer:

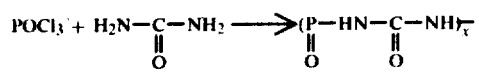

Urea (4.75 g.) and phosphorus oxychloride (7.6 g.) are heated in a 50 ml. round bottom flask with magnetic stirring under a condenser for three hours. After the reaction is complete, the contents of the flask are maintained at 130° C. for an additional two hours, heated to 250° C. for an additional ½ hour, and then held at 250° C. under reduced pressure for another ½ hour. The product is scraped from the flask, pulverized and washed with ether and dried.

In accordance with the procedures of Example 1, when 1.0 gms. of the above polymer is heated with 7.6 gms. of CoCl$_2$, the resulting product may be worked up to provide the corresponding cobalt catalyst.

PREPARATION OF OXIDATION CATALYST WITH METAL SALTS PRESENT DURING THE POLYMERIZATION

Example 4

Phosphine-urea Polymer:

$$NiCl_2 + PCl_3 + H_2N-\underset{\underset{O}{\|}}{C}-NH_2 \longrightarrow$$

$$(P-NH-\underset{\underset{O}{\|}}{C}-NH)_x \cdot [NiCl_2]$$

A mixture of 6.5 g. of NiCl$_2$, 9.7 g. of PCl$_3$ and 4.6 g. of urea is pulverized together in a glass motar. The resulting powder is placed in a 50 ml. flask fitted with a condenser and a thermometer and heated until the PCl$_3$ begins to reflux at about 75° C. Eventually the temperature is raised to 190° C. and held there for about three hours. After cooling, the sample is removed and extracted in a Soxhlet extractor with water to remove any unreacted materials, removed and dried overnight.

Example 5

Phenylphosphonic Dichloride-urea Polymer:

$$Cl-\underset{\underset{\phi}{|}}{\overset{\overset{O}{\|}}{P}}-Cl + H_2N-\underset{\underset{O}{\|}}{C}-NH_2 + NdCl_3 \longrightarrow$$

$$(\underset{\underset{\phi}{|}}{P}-HN-\underset{\underset{O}{\|}}{\overset{\overset{O}{\|}}{C}}-NH)_x \cdot [NDCl_3]$$

In accordance with the procedure of Example 4, the neodymium chloride (12.5 g.) is mixed with urea (3.0 g.) first and then reacted with phenylphosphonic dichloride (9.73 g.). The temperature is raised to 230° C. over a 2 hour period and then maintained at 230° C. for an additional 2 hours. A final heating of about 15 minutes duration under reduced pressure is used to aid in removal of gaseous reaction products. The product obtained on cooling the reaction vessel is pulverized and extracted with water in a Soxhlet extractor to remove any excess metal chloride.

In accordance with the above procedure, but using copper chloride as the metal salt, a copper-containing polymer is formed which gives an elemental analysis the following: C, 27.1; H, 2.72; Cu, 23.87. Calculated values assuming a 1:1-Cu:polymer complex are: C, 26.6; H, 2.22; Cu, 25.9.

Example 6

Phosphonyl-ethylene Diamine Polymer:

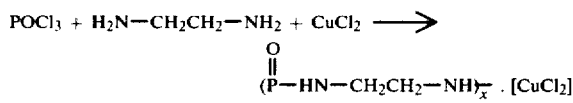

Copper chloride (6 g.) is added to a 50 ml. round bottom flask fitted with a condenser and a thermometer. The phosphonyl chloride (9.7 g.) is added through the condenser followed by the ethylene diamine (3.0 g.). After the initial reaction exotherm has subsided, the temperature is raised to about 115° C. The product obtained on cooling is worked up as described in the previous example.

Example 7

Phenylphosphoric Dichloride-Ethylene Diamine-Cobalt Chloride Polymer:

Six grams of cobalt chloride salt is placed in the equipment described in the proceeding example. 9.7 gms. of phenylphosphoric dichloride and 3.0 gms. of ethylene diamine are added sequentially via the condenser. A rapid exothermic reaction is observed with a temperature rise to 110° C. The temperature is raised with a heater to 220° C. over a period of 3 hours. After cooling the reaction product is cooled, crushed, and water extracted overnight, and dried in an oven at 115° C.

Example 8

Preparation of Copper Poly($\beta$-alanine) Catalyst: (Condensation-Type Polymerization)

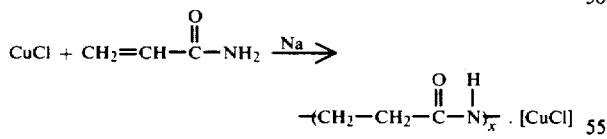

A solution of 4.4 g. (0.062 moles) of acrylamide in 4 ml of dimethylformamide is prepared in a 50 ml. round bottom flask which is swept continually with nitrogen. After adding 6.0 g. (0.06 moles) of cuprous chloride, the solution is heated to about 100° C. and 2 drops of a sodium dispersion in xylene is added to initiate polymerization. The reaction is rapid and after about 10 minutes the solution is carefully quenched with water. The metal-containing polymer is filtered and then extracted continuously overnight with water to remove any uncomplexed metal ions. The polymer is then dried under vacuum and pulverized.

Example 9

Preparation of Iron-Polyacrylamide: (Addition Polymerization)

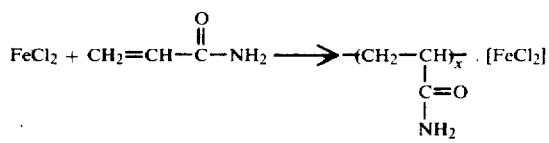

In a large three-necked flask equipped with a stirrer, thermometer and gas inlet tube are placed 51.8 g. acrylamide and 414.7 g. distilled water. This solution is heated with stirring to 70° C. under carbon dioxide and 65 g. of ferrous chloride are carfully added. 7.7 g. of isopropyl alcohol and 0.1 g. potassium persulfate are then added. The reaction solution is warmed up to about 80° C. and this temperature is maintained for 2 hours. The product polymer is isolated by precipitation in methanol, washed with methanol and dried under vacuum.

Example 10

Preparation of Iron-Poly(4,4'-oxydiphenylurea/2,4-toluene urea):

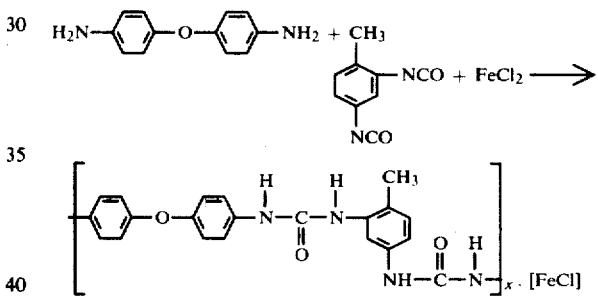

In a 100 ml. three-necked round bottom flask equipped with a stirrer is placed 5.0 g. (0.025 moles) of 4,4'-diaminodiphenylether in 25 ml. of dimethylforamide. To this solution is first added 3.8 g. (0.03 moles) of ferrous chloride (anhydrous), and then a solution of 4.35 g. (0.025 moles) of 2,4-toluenediisocyanate in 25 ml. of dimethylformamide as it has been prepared. The reaction is stirred for ½ hour and then warmed to 50° C. for an additional ½ hour. The metal-containing polymer is isolated by pouring the reaction mixture into cold water with rapid stirring. The product polymer is extracted with water overnight to remove any uncomplexed iron salt, dried and further pulverized.

Example 11

Preparation of Poly (hexamethylene adipamide)

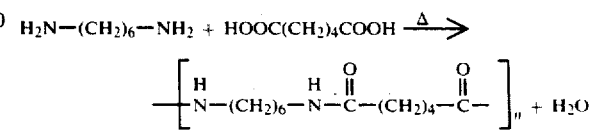

Adipic acid (0.100 mole), 14.6 g.) is dissolved in a flask in about 100 mls. of ethanol (dry) by the application of gentle heating and then cooled. To this solution is added a solution of 11.8 g. (0.012 mole) of hexamethylene diamine dissolved in 25 ml. of absolute ethanol. After mixing and cooling overnight, the crystals are filtered and washed with cold absolute ethanol and dried. The dried crystals are then charged to a heavy-walled polymerization tube, the tube sealed and heated at about 220° C. for one to two hours. Normal safety precautions are advised for working with glass tubing under pressure. After the heat treatment has been completed and the tube cooled, it is carefully opened and then reheated to 270° C. under vacuum until the rise of water vapor bubbles in the melt indicates that the polymer has reached maximum viscosity. The opaque white polymer which forms on cooling is removed by breaking the tube.

A catalyst may be formed by reheating the polymer (1 g.) until it fuses in the presence of 0.7 g. of anhydrous nickel chloride, cooling the mixture, extracting the powdered melt for several hours to remove excess salt, then filtering and drying overnight in a vacuum dessicator.

Example 12

Preparation of Polyhexamethylenesebacamide

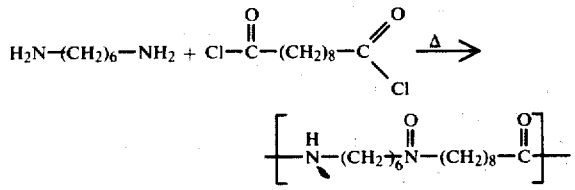

To a solution of freshly distilled sebacoyl chloride (3 mls. in 100 mls. of freshly distilled tetrachloroethylene) in a 200 ml. beaker is carefully added a solution of 44 g. hexamethylenediamine in 50 mls. of water. The polymeric film which forms at the interface of the two solutions is pulled from the beaker continuously until no more forms. The formed polymer is washed with acetone and dried in a vacuum oven.

To prepare a catalyst, 2.0 g. of the above polymer is heated above its melt temperature (215° C.) with 0.75 g. of anhydrous copper chloride for 3 hours and with occasional stirring. After cooling, the solid is pulverized, extracted with water continuously for several hours and then dried in a vacuum over at 50° C. overnight.

Example 13

Preparation of Poly(decamethyleneoxamide)

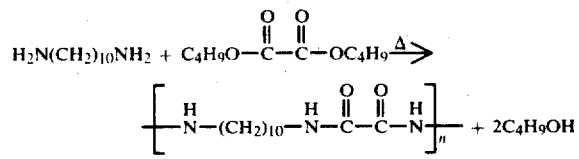

In dry toluene (25 mls.) is dissolved 0.1 mole (17.23 g.) decamethylenediamine, and to this solution contained in a 3-necked 250 ml. flask equipped with a stirrer, drying tube and nitrogen inlet tube is added at one time 0.1 mole (20 g.) of dibutyl oxalate, the entire operation being carried out under an inert gas. Stirring is begun and white solid soon forms; stirring is continued until the mass is too thick to stir. Two hours later, the mass is heated to 270° C. under an inert atmosphere. During this period, the toluene distills off. The reaction mass is kept at 270° C. for one hour, then cooled whereupon the white polymeric mass forms.

A catalyst can be prepared from this polymer by reheating the white mass in the presence of an equivalent amount of cobalt chloride (anhydrous), cooling, crushing the resulting solid and after extracting the excess salt drying in a dessicator.

Example 14

Preparation of Poly(hexamethylene-m-benzenedisulfonamide)

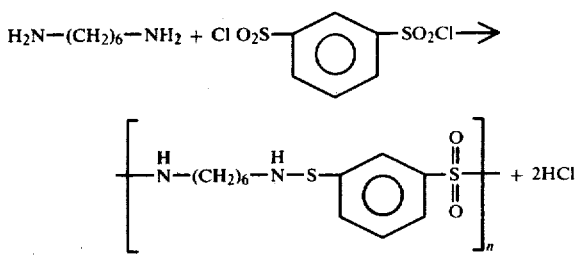

To a stirred solution of 145 mls. of distilled water, 20 mls. of 10% aqueous Duponol, 5.30 g. of sodium carbonate, and 3.02 g. of hexamethylenediamine is added over a period of about ½ minute 6.88 g. of m-benzenedisulfonyl chloride in 200 ml. of methylene chloride. After stirring for 15 minutes, 100 ml. of absolute ethanol is added all at once. The solid is filtered, washed with water, ethanol, acetone, hot water and finally with acetone again. The polymer is dried at 70°-75° C. in a vacuum oven overnight.

An active catalyst can be prepared from the above polymer according to the procedure given in Example 13, except that the heating temperature in this case is about 200° C. and manganese chloride substituted for the metal salt of that example.

Example 15

Preparation of Polyacrylamideoxime

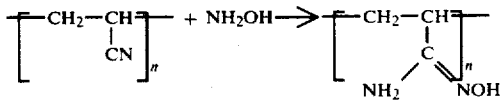

Polyacrylonitrile 5.0 g. is added to 30 ml. of dimethylformamide in a 200 ml., 3-necked flask equipped with a stirrer and held at 75° C. Two g. of hydroxylamine hydrochloride and 1.5 g. of sodium carbonate (anhydrous) are added and the resulting mixture heated with stirring for 1 hour. The polymer is then precipitated by addition of excess methanol, filtered, washed with more methanol and dried.

A catalyst may be prepared from this polymer according to the procedure of Example 13 using ferric chloride as the metal salt. Alternatively, the polymer may be dissolved in dilute hydrochloric acid and the ferric chloride added to this solution. The polymer assumes a deep red-to-violet color upon addition of the ferric chloride which is characteristic of the ferric complex of the amideoxime group. The polymeric catalyst can be precipitated from solution by the addition of excess methanol and washed and dried in the usual manner.

Example 16

Preparation of Poly(2,2'-dimethoxy-4,4'-biphenylene carbodiimide)

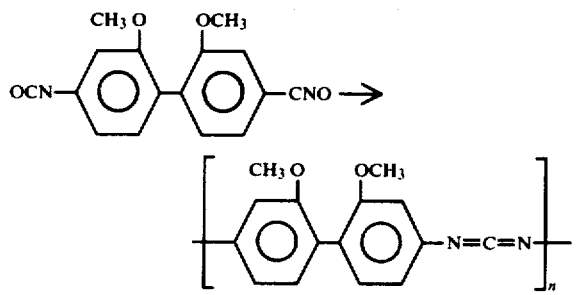

Ten g. of 2,2'-dimethoxy-4,4'-biphenylene diisocyanate is dissolved in 100 ml. of hot (100° C.) xylene. The solution is polymerized using 0.04 g. of 1-ethyl-3-methyl-3-phospholene oxide in a flask with refluxing and stirring (4–6 hrs.). The white powdered polymer is filtered, washed with benzene and dried.

A catalyst can be prepared from this polymer by heating a mixture of the powdered polymer with neodymium chloride until the melt point is reached. The catalyst is then cooled, powered, extracted with water, and dried in a vacuum oven.

Example 17

Preparation of Poly(N,N'-phthaloyl-trans-2,5-dimethylpiperazine)

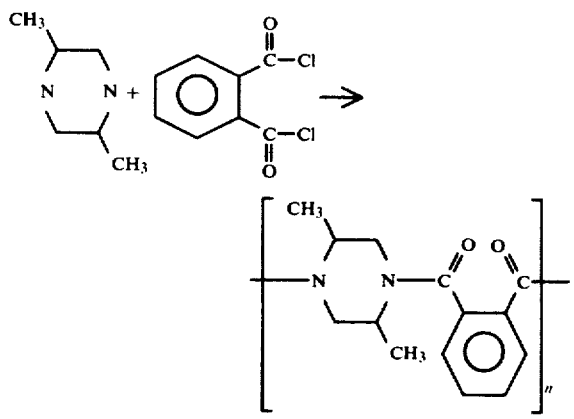

In an efficient mixer is placed 6.5 g. (0.058 mole) of trans-2,5-dimethylpiperazine, 25 ml. methylene chloride, 20 ml. of 5% Duponol solution, and 150 ml. of ice water containing 0.1 mole of sodium hydroxide. To the rapidly stirred system is added at one time 7.2 ml. of phthaloyl chloride in 25 ml. of methylene chloride. The mixture is stirred for 10 minutes, then poured into one liter of water; the methylene chloride is boiled off on a steam bath. The polymer is filtered, washed with 200 mls. of water three times and dried in a vacuum over at 70° C.

A catalyst is prepared from the polymer according to the instructions in Example 13 by heating to 360° C. with an equivalent amount of cobalt chloride.

DESCRIPTION OF THE OXIDATION PROCESS

The process of this invention employing the above-described types of catalysts is conveniently carried out by the rapid passage of air or oxygen through a suitable reactor, to which has first been added the starting material and catalyst. Solvents which are inert to the reaction may be employed if desired.

The air or oxygen should be brought into intimate contact with the liquid phase with vigorous agitation either mechanically by the use of high speed stirrers, or by aeration using suitable nozzles or the like.

Mechanical agitation has been found to be particularly effective in those cases where the rate at which the oxygenating gas is introduced into the reactor is low, i.e., below about 3 liters per hour. Thus, for example, when air is merely introduced at the surface of the reaction mixture, agitation by a commercially available reciprocating disc type stirrer (e.g., "Vibro-Mixer", Chemapec Company, Inc., Hoboken, New Jersey) has been found to increase the rate of oxidation per hour by as much as four-fold over what is obtained with lesser amounts of agitation.

Alternatively, these increased rates may similarly be achieved, and mechanical agitation substantially or entirely dispensed with by appreciably increasing the rate at which air or oxygen is introduced into the reaction medium. This is preferably accomplished by bubbling the oxygenating gas through the reaction mixture, vigorously, desirably in such a manner as to insure maximum dispersal of the gas through the medium, as for example, by using fritted glass discs or the like. Depending upon the amount of liquid medium involved, the rate of oxygenating gas may generally vary from about 3 to 300 liters per hour.

The amount of catalyst employed will vary depending upon the nature of the catalyst itself. In general, however, from about 0.01 to 5.0 parts by weight of catalyst per 100 parts of substrate, and preferably from 0.2 to 1.0 parts per 100 parts has been found to be satisfactory.

The rate of input of oxygen or air will likewise vary depending upon the reaction temperature and pressure employed. There should be provided an amount at least theoretically sufficient to convert the alkylaromatic compound to the corresponding hydroperoxide, and preferably an excess of this amount. In general, a flow rate ranging from 0.5 to 300 liters per hour is sufficient for most conversions, and preferably at least 3 liters per hour as described above. While the reaction is preferably carried out at atmospheric pressure, it is possible to employ an oxygen pressure of from about 0.2 atmospheres to 50 atmospheres, and preferably about 1 to 10 atmospheres. At these higher pressures the oxidation rate is found to increase substantially when the polymeric complexes are employed, and particularly those catalysts which are selective for hydroperoxide formation.

The reaction temperature may range from about 80° to 200° C. and preferably from 90° to 150° C.

The reaction is generally run for from half an hour to ten hours, depending upon the amount of substrate employed and the degree of conversion desired. When, however, a hydroperoxide is the principal product being recovered, it is desirable that the reaction be terminated after a period of one to six hours at which point the reaction rate usually begins to taper off.

The compounds which may be oxidized in accordance with the present invention are, as mentioned above, those organic compounds containing activated carbon-hydrogen bonds. That is to say, they include those hydrogen-containing carbon atoms, and particularly methylene and methine groups, which are adjacent certain activating groups. These activating groups include such groups as —CH=CH—, —OR, —NO₂, halo, phenyl and the like, where R is alkyl or cycloalkyl.

Included amongst the starting materials which are of particular use in this process are any straight or branched chain unsaturated olefins having at least one hydrogen atom on the α carbon atoms, such as octene-1 and the like, as well as cyclic olefins having at least one hydrogen atom on the α-carbon atom, such as cyclohexene, cyclooctadiene, α-pinene, dl-limonene and the like. These olefins may contain substituent groups which are non-reactive under conditions of this process, as for example ester, halo, nitro, alkyl or like groups which remain as substituents of the final product.

Also included as preferred starting materials in this process are secondary and tertiaryl alkyl aromatic hydrocarbons having the structural formula:

wherein R is lower alkyl; R₁ is lower alkyl or hydrogen; Ar is a substituted or unsubstituted aromatic nucleus such as phenyl or naphthyl; and wherein R and R₁ may be the same or different alkyl groups. The aromatic nucleus may be substituted by such groups as lower alkyl, lower alkoxy, halo, nitro or cyano radicals. Preferably, the secondary or tertiary alkylaromatic hydrocarbon is represented by such compounds as cumene, ethylbenzene or sec.-butylnaphthalene, although it is understood that compounds such as n-butylbenzene, sec.-butylbenzene, isopropylnaphthalene and the like may also be employed. The lower alkyl groups may contain from 1 to 12 carbon atoms.

Many of these polymer.metal complexes preferentially give yields of hydroperoxides to the exclusion of other oxidation products at conversion rates of at least about 3 to 8 percent per hours. Advantageously, small amounts of a hydroperoxide, preferably one corresponding to the desired product, may be introduced into the reaction medium to act as a reaction initiator. Thus, for example, when cumene is being oxidized, it has been found to be advantageous to add small amounts of cumyl hydroperoxide in order to further accelerate the initial rate of reaction. The amount of hydroperoxide to be added is not critical, but 0.1 percent to 1.0 percent by weight of the starting material is preferred.

As mentioned hereinabove, the oxidation products of the instant process are hydroperoxides, or the decomposition products thereof, i.e. alcohols, ketones, aldehydes, epoxides or mixtures thereof. Of these various products, maximization of the formation of the hydroperoxides is generally preferred inasmuch as those compounds derived from the alkylaromatic compounds are especially useful as intermediates in the prepartion of such products as phenols, naphthols, acetone and the like, while those derived from, e.g., the olefin hydroperoxides, are useful in facilitating the drying capabilities of polymers, i.e., they are useful as siccative agents.

In the case of those remaining metals which yield little or no detectable amounts of hydroperoxides in the final product, but rather other oxidation products, this is because the hydroperoxides are rapidly decomposed by the catalyst complex itself to form aldehydes, alcohols, ketones or the like. That is to say, since the known mechanism for the autoxidation of alkyl aromatic compounds includes the homolytic cleavage of the first formed intermediate, i.e. the hydroperoxide, it is recognized that catalysts which accelerate this oxidation will also accelerate the decomposition of this intermediate. Hence it is possible to autoxidize the hydrocarbon to oxidized products without being able to detect the hydroperoxide intermediate because it is being decomposed to other oxidation products as rapidly as it is being formed. Therefore, the fact that no hydroperoxide is detected in the product does not mean it was not formed; it simply means that the catalyst is very effective in further converting this intermediate to aldehydes, ketones, alcohols, etc. In fact, the participation of hydroperoxides in the autoxidation of these hydrocarbons is so well established in the chemical literature that no other mechanistic pathways are seriously considered. See, for example, G. A. Russell, J.A.C.S. 77, 4583–4590, (1955); H. S. Blanchard, J.A.C.S. 82, 2014–2021, (1959); J. A. Howard, et al., *Canadian Jour. Chem.* 45, 785–792 (1966); inter alia.

Thus, it will be evident to those skilled in the art that the exact nature of the oxidation product can readily be determined by routine experimentation with various catalyst, but in all cases it will be either an hydroperoxide and/or the decomposition products thereof as shown in the above-cited art.

The resulting products are readily recovered from the reaction medium by conventional methods. Thus, for example, as hydroperoxide may be conveniently recovered by isolating it as its sodium salt by addition of concentrated aqueous NaOH to the reaction product, followed by separation and drying of the hydroperoxide salt.

The catalyst complexes of this invention are solid materials, even under the reaction conditions of this process, and, in fact, are insoluble in the oxidation product. They may, therefore, be readily recovered from the reaction mixture by simple filtration methods.

In the following examples, unless otherwise noted, both rate of conversion of the starting material and selectivity of the catalyst for converting the starting material to the corresponding hydroperoxide are measured. To measure rate of conversion, regardless of the nature of the oxidation product, the amount of oxygen uptake in a closed system is used; to measure the amount of hydroperoxide formed, samples of the reaction medium are perodically withdrawn and iodometrically titrated to determine the hydroperoxide content. On the basis of both of these figures, the selectivity of any given catalyst for the formation of hydroperoxide can then be routinely determined.

EXAMPLE 18

In a standard reaction, 200 m moles (24.0 g) of neat cumene is oxidized in a 100 ml. resin flask reactor immersed in a temperature-regulated oil bath at 100° C. The catalyst is used at the 0.1 mole percent level. 2 m moles of cumene hydroperoxide initiator are added to eliminate the induction period. The rate of oxidation is followed by measuring the uptake of oxygen by means of a calibrated pressure transducer connected to a recorder. Agitation is provided by a Vibromixer. Periodically samples are withdrawn and their hydroperoxide content determined iodometrically. The oxygen uptake is regarded as a measure of the degree of conversion of the substrate, and the hydroperoxide content divided by the oxygen uptake is useful as a measure of the selectivity of the catalyst for hydroperoxide.

The following table illustrates the results obtained from cumene oxidations using the catalysts of this invention. Dramatic increases in the rate of oxidation are evident. All reactions are carried out in the manner described above.

containing backbone, said backbone containing functional groups which are complexed with a metal of any of Group IB to VIIIB, or IIA of the Periodic Table, said polymer being further characterized in being insoluble under the conditions of said process.

2. The process according to claim 1 wherein the functional groups are incorporated in the backbone of the polymer.

3. The process according to claim 1 wherein the functional groups are incorporated in pendant side chains attached to the backbone of the polymer.

4. The process according to claim 1 wherein the oxidation is carried out in the presence of a hydroperoxide initiator.

TABLE I

| Polymer-Ligand | Metal | Prep. Method | 1 Hour % Conv. | 1 Hour % Select. | 2 Hours % Conv. | 2 Hours % Select. | Final Hours | % Conv. | % Select. |
|---|---|---|---|---|---|---|---|---|---|
| None-Thermal Oxidation 100° C. | None | — | 0.43 | 100 | 1.10 | 100 | 7 | 9.7 | 92 |
| O=P(H)(O)–N(H)–C(=O)–N(H)– | Ni | Fusion | 3.8 | 93 | 10.1 | 87 | 4 | 17.5 | 73 |
| " | Co | Fusion | 3.8 | 93 | 8.6 | 87 | 5 | 18.1 | 89 |
| " | Cu | Fusion | 3.1 | 87 | 7.4 | 83 | 4 | 16.1 | 82 |
| " | Co | Polymerization | 4.3 | 91 | 9.0 | 89 | — | — | — |
| " | Cu | Polymerization | 11.4 | 84 | 22.6 | 86 | 3 | 33.0 | 80 |
| " | Nd | Polymerization | 12.0 | 74 | 22.2 | 73 | 5 | 45.7 | 66 |
| –P(O)(H)–N(H)–C(=O)–N(H)– | Ni | Polymerization | 7.3 | 80 | 15.0 | 82 | 3 | 20.8 | 84 |
| –P(=O)(H)–N(H)–C(=O)–N(H)– | Co | Polymerization | 4.3 | 74 | 9.3 | 78 | — | — | — |
| | Ni | Polymerization | 12.1 | 53 | 21.6 | 62 | 4 | 37.3 | 67 |
| | Cu | Polymerization | 14.7 | 51 | 26.3 | 58 | 4 | 44.7 | 58 |
| –P(H)–N(H)–C(=O)–N(H)– | Ni | Polymerization | 5.8 | 80 | 10.9 | 80 | 4 | 19.4 | 86 |
| O=P(H)(φ)–N(H)–CH$_2$CH$_2$–N(H)– | Cu | " | 12.8 | 82 | 25.6 | 76 | 4 | 43.0 | 74 |
| O=P(H)–N(H)–CH$_2$CH$_2$–N(H)– | Cu | " | 5.0 | 90 | 9.4 | 88 | — | — | — |

We claim:

1. In a process for the oxidation of olefins having from 3 to 20 carbon atoms, or organic compounds of the formula $$R_1-\underset{\underset{Ar}{|}}{\overset{\overset{R}{|}}{C}}-H$$

wherein R is lower alkyl; R$_1$ is lower alkyl or hydrogen; and Ar is naphthyl or phenyl, wherein R and R$_1$ may be the same or different, to form a reaction mixture comprising the corresponding hydroperoxides, the decomposition products of said hydroperoxides, or mixtures thereof, the improvement which comprises contacting said compounds with air or oxygen at temperatures of from about 80° to 200° C. in the presence of a catalyst comprising a water-stable polymer having a nonmetal- 5. The process according to claim 1 wherein the polymer is a phenylphosphonic diahalide-urea polymer.

6. The process according to claim 1 wherein the polymer is a phenyldihalophosphine-urea polymer.

7. The process according to claim 1 wherein the polymer is a phosphonyl-urea polymer.

8. The process according to claim 1 wherein the polymer is a phosphine-urea polymer.

9. The process according to claim 1 wherein the complexed metal of the polymer is nickel, copper, cobalt, iron or neodymium.

10. The process according to claim 1 wherein the catalyst is formed by preparing the polymer is the presence of a metal salt.

11. The process according to claim 1 wherein the catalyst is prepared by preparing the polymer in the absence of a metal salt, followed by reaction of the polymer with the metal salt.

* * * * *